United States Patent [19]

Wang et al.

[11] 4,080,361

[45] Mar. 21, 1978

[54] SYNERGISTIC COMBINATION OF ALKOXY-SUBSTITUTED PHOSPHONITRILIC COMPOUNDS AND ORTHO-HINDERED PHENOLIC ANTIOXIDANTS

[75] Inventors: Richard H. S. Wang; Gether Irick, Jr., both of Kingsport, Tenn.

[73] Assignee: Eastman Kodak Company, Rochester, N.Y.

[21] Appl. No.: 741,905

[22] Filed: Nov. 15, 1976

[51] Int. Cl.$^2$ .............................................. C08K 5/51
[52] U.S. Cl. ........................... 260/45.9 NP; 252/404; 260/45.8 NT; 260/45.8 R; 260/45.85 B; 260/45.95 C; 260/45.95 R; 260/45.95 H; 260/927 N
[58] Field of Search ............... 260/45.9 NP, 45.8 NT, 260/45.95 B, 45.95 D, 45.95 C, 45.95 R, 45.95 H, 45.85 B, 45.75 N, 927 N; 252/404

[56] References Cited

U.S. PATENT DOCUMENTS 3,840,621  10/1974  Franko-Filipasic ................... 260/927
3,920,616  11/1975  Murch ........................... 260/45.9 NP

FOREIGN PATENT DOCUMENTS 162,532  10/1964  U.S.S.R.

OTHER PUBLICATIONS

CA 63 5517f (1965).
J. Org. Chem. 31 (6) 2004–2005 (1966).
Index Chemicus 22 69578 (1966).

*Primary Examiner*—V. P. Hoke
*Attorney, Agent, or Firm*—J. Frederick Thomsen; Daniel B. Reece, III

[57] ABSTRACT

A stabilizer combination for use in improving the resistance of olefin polymers to deterioration and physical properties on exposure to heat comprising A) an organic phosphonitrilic composition derived from a triphosphonitrilic halide and an hydroxy compound selected from alcohols containing one to about 20 carbon atoms and diols having the formula

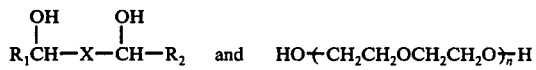

wherein X is a covalent bound or alkylene of 1 to about 12 carbon atoms, $R_1$ and $R_2$ are the same or different as hydrogen or alkyl having 1 to about 6 carbon atoms, and n is an integer from 1 to about 200; and B) from about 0.1 to about 25 parts by weight of an ortho-hindered phenolic primary antioxidant.

7 Claims, No Drawings

SYNERGISTIC COMBINATION OF ALKOXY-SUBSTITUTED PHOSPHONITRILIC COMPOUNDS AND ORTHO-HINDERED PHENOLIC ANTIOXIDANTS

This invention relates to improved polyolefin compositions. More particularly, it relates to polyolefin compositions having greatly increased resistance to light and thermal degradation. Polymeric materials, particularly polyolefins, are commonly subjected to elevated temperatures in the course of their processing and application as useful items of commerce. To minimize deterioration in polymeric materials, antioxidants, or stabilizers are often incorporated therein. This invention provides new synergistic combinations of stabilizers which improve the stability of polyolefins and particularly polypropylene and polyethylene against deterioration resulting from oxidation at elevated temperatures. These synergistic combinations of stabilizers comprise a conventional ortho-hindered phenolic primary antioxidant and a compound derived from an organic phosphonitrilic halide and specific hydroxy compounds.

Accordingly, there is provided a stabilizer combination for use in improving the resistance of olefin polymers to deterioration in physical properties on exposure to heat comprising A) from about 0.1 to about 25 parts by weight of an organic phosphonitrilic composition derived from a triphosphonitrilic halide and a hydroxy compound selected from alcohols containing 1 to about 20 carbon atoms, and diols having the formula

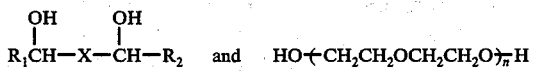

wherein X is a covalent bond or alkylene of 1 to about 12 carbon atoms, $R_1$ and $R_2$ are the same or different as hydrogen or alkyl having 1 to about 6 carbon atoms, and n is an integer from 1 to about 200; and B) from about 0.1 to about 25 parts by weight of an ortho-hindered phenolic primary antioxidant.

The olefin polymers which can be stabilized by the combinations of this invention are those polymers and copolymers prepared from olefin monomers having from 2 to about 10 carbon atoms. Examples of these polyolefins are polyethylene, polypropylene, polyallomer, polybutylene, polypentene, polyoctene, and the like. The preferred polyolefins useful in the practice of this invention are polypropylene and polyethylene of varying densities.

The ortho-hindered phenolic antioxidants useful in the practice of this invention are well known in the art. Examples of these compounds are as follows:

1. 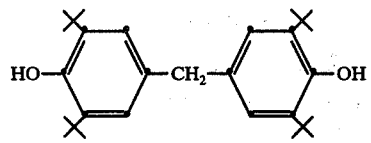

2. 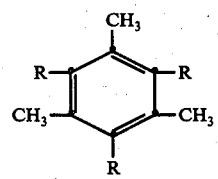

3. 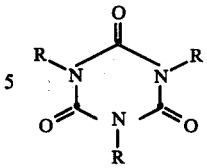

4. 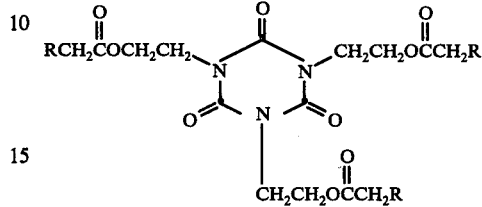

5. 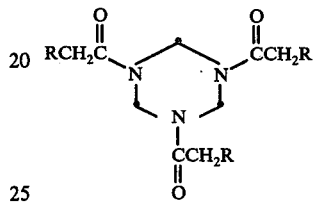

6. 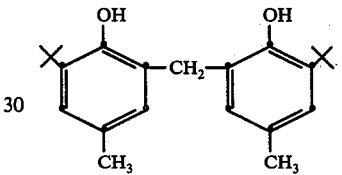

7. 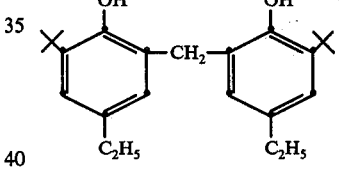

8. 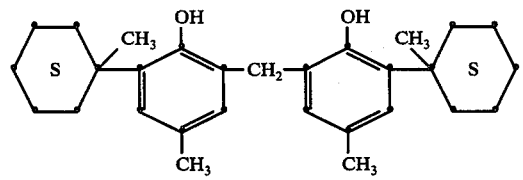

9. 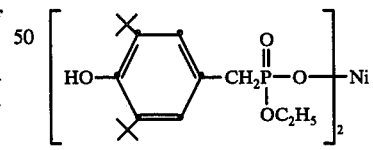

10. 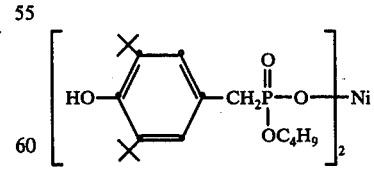

11. 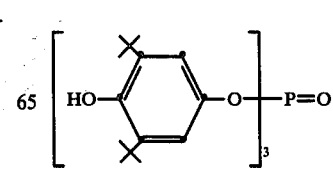

3

-continued

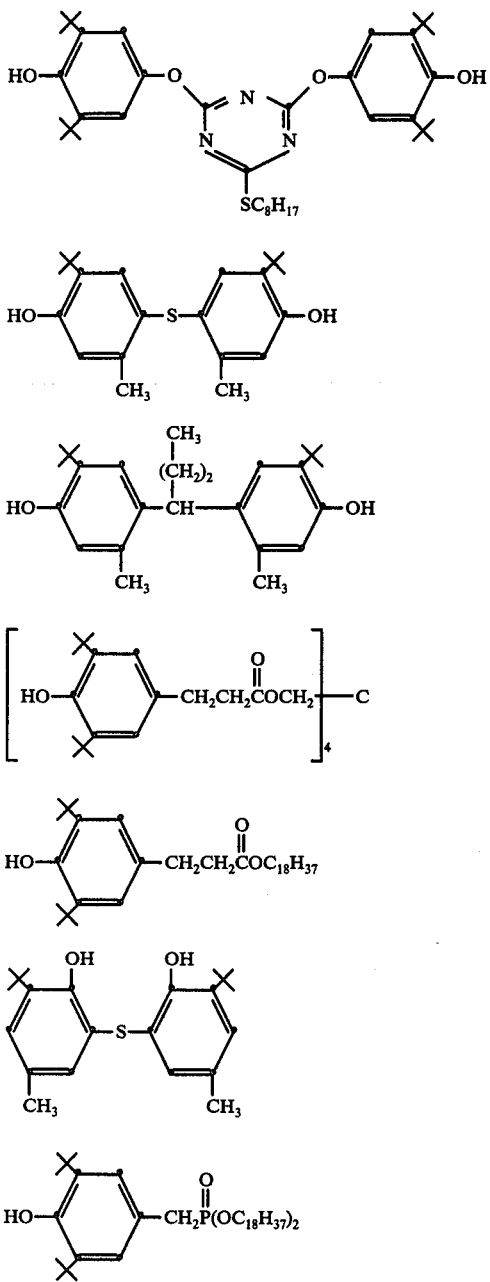

wherein

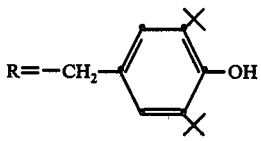

In a preferred embodiment of the invention the ortho-hindered phenolic antioxidant which is most advantageously utilized in combination with the phosphonitrilic compounds of this invention are identified as Nos. 2, 3, 13, 15, 16 and 19.

The phosphonitrilic compounds found to be useful in the practice of this invention are those derived from a triphosphonitrilic halide and a hydroxy compound selected from alcohols containing 1 to about 20 carbon atoms, and diols having the formula $$\begin{array}{cc} \underset{|}{OH} & \underset{|}{OH} \\ R_1CH-X-CH-R_2 \end{array} \quad \text{and} \quad HO(CH_2CH_2OCH_2CH_2O)_nH$$

wherein X, $R_1$ and $R_2$ and n are defined above. Examples of the triphosphonitrilic halides useful in the practice of this invention are among others triphosphonitrilic chloride and triphosphonitrilic bromide. Examples of suitable alcohols useful in the preparation of the compounds of this invention are methanol, ethanol, propanol, isopropanol, butanol, octanol, n-decanol, 2-decanol, 3-decanol, octadecanol, 2-ethylhexanol, and the like. Examples of suitable glycols or diols which can be utilized in the preparation of the compounds of this invention are ethylene glycol, propanediol, butanediol, neopentyl glycol, and the like.

The amount of Components A and B used in the compositions of this invention should each be present in amounts sufficient to enhance the stabilizing effect of the other to obtain the desired synergistic effect. Generally, advantageous results occur when from about 0.1 to about 25 parts by weight of each of the components based on the weight of the amount of polyolefin are utilized is sufficient. Preferably, from 0.1 to about 10 parts by weight of each of the components is utilized for best results.

In addition, there can also be incorporated into the polymers of this invention from 0.1 to about 25 parts per hundred parts of polymer of additives that may generally be incorporated into polyolefins such as carbon black, other stabilizers, secondary antioxidants (e.g., esters of thiodipropionic acid), talc, titanium dioxide, silicas, metal deactivators, slip agents, flame retardant additives, coloring agents, anti-fungal agents, etc.

This invention will be further illustrated by the following examples although it will be understood that these examples are included merely for purposes of illustration and are not intended to limit the scope of the invention.

EXAMPLE 1

Preparation of tris(ethylenedioxy) cyclotriphosphazene, Ia: A solution of 22.5 g. (0.36 mole) of ethylene glycol in 300 ml of pyridine was mixed with 23.4 g. (0.06 mole) of triphosphonitrilic chloride. The mixture was stirred for 30 minutes and then held at room temperature for 20 hours. The product was filtered and washed with water, ethylene alcohol, and methylene chloride (yield: 60%). Found (and calcd. for $C_6H_{12}N_3O_6P_3$/M.W. 315): C 22.7 (22.90); H 3.77 (3.84); N 13.30 (13.34); and P 27.27 (29.49).

EXAMPLE 2

Preparation of hexakis(butoxy)cyclotriphosphazene, Ib: To a chilled solution (0°–5° C.) of triphosphonitrilic chloride (0.018 mole) in 26 ml of pyridine, butanol (0.34 mole) was added. The mixture was stirred at room temperature overnight, diluted with petroleum ether and washed with dilute HCl, NaHCO₃, and water successively. After removal of solvent, the product IIa was obtained in a yield of 90%. Found (and calcd. for $C_{24}H_{54}N_3O_6P_3$/M.W. 574): C 47.32 (50.25); H 9.00 (9.49); and N 7.71 (7.33).

EXAMPLE 3

Evaluation of stabilizers in polyethylene and polypropylene: The results of oven tests for compounds Ia and Ib as synergists with phenolic antioxidants in polyethylene and polypropylene are shown in Tables 1 and 2.

The formulations were prepared by dry-blending the components, milling on an open two-roll mill and pressing films of 5-mil thickness. Films were then suspended in a 140° or 160° C. oven until embrittlement occurred.

Table 1
Effectiveness of Antioxidants in Polypropylene

| | | Oven Life (Hour) for 5-Mil Film at 140° C. Duplicate Evaluations | |
|---|---|---|---|
| | Antioxidant | A | B |
| 1. | None | <1 | <1 |
| 2. | 0.3% DLTDP[1] | 100 | — |
| 3. | 0.3% Weston 618[2] | <1 | — |
| 4. | 0.3% Ia | <1 | <1 |
| 5. | 0.3% Ib | <1 | — |
| 6. | 0.05% Irganox 1010[3] | 560 | — |
| 7. | 0.10% Irganox 1010 | — | 900 |
| 8. | 6 + 2 | 870 | 640 |
| 9. | 7 + 2 | — | 1350 |
| 10. | 6 + 3 | 970 | — |
| 11. | 6 + 4 | 1710 | 2280 |
| 12. | 6 + 5 | 300 | — |
| 13. | 7 + 4 | — | 2700 |
| 14. | 6 + 0.1% Ia | 1150 | — |
| 15. | 0.03% Irganox 1010 + 4 | 1140 | — |
| 16. | 0.05% Goodrite 3114[4] | 50 | — |
| 17. | 16 + 2 | 590 | — |
| 18. | 16 + 3 | 250 | — |
| 19. | 16 + 4 | 2100 | — |
| 20. | 16 + 5 | 50 | — |
| 21. | 0.05% Ethyl A.O. 330[5] | 530 | — |
| 22. | 21 + 2 | 710 | — |
| 23. | 21 + 3 | 640 | — |
| 24. | 21 + 4 | 1810 | — |
| 25. | 21 + 5 | 540 | — |

[1]Dilauryl 3,3'-thiodipropionate (from American Cyanamid Co.)
[2]Distearyl pentaerythritol diphosphite (a trademark of Borg Warner Corp.)
[3]Tetrakis[3-(3,5-di-tert-butyl-4-hydroxyphenyl)propionyloxymethyl]-methane (a trademark of Ciba Geigy)
[4]1,3,5-Tris(3,5-di-tert-butyl-4-hydroxybenzyl)isocyanurate (a trademark of Goodrich Co.)
[5]2,4,6-Tris(3,5-di-tert-butyl-4-hydroxybenzyl)mesitylene (a trademark of Ethyl Co.)

It is apparent from a comparison of the oven lives of polypropylene formulations (Table 1) that phosphorus compounds by themselves are not effective stabilizers. For instance, $I_a$, $I_b$ and Weston 618 (Items 3, 4, 5) do not significantly increase the lifetime of the unstabilized polypropylene (Item 1). Also, hindered phenolic antioxidants alone provide only moderate increases in polypropylene stability. For instance, 0.05% of Irganox 1010, Goodrite 3114 or Ethyl A.O. 330 (Items 6, 16 and 21) provided lifetimes of only 560, 50 and 530 hrs. respectively. Increasing the concentration of Irganox 1010 to 0.1% only gave a lifetime of 900 hrs. Very long lifetimes were only attainable by a combination of the phosphorus compounds of this invention in combination with hindered phenolic antioxidants. For instance, a combination of 0.05% Irganox 1010 with 0.3% $I_a$ gave a lifetime of 1710–2280 hrs. (Item 11); 0.1% Irganox 1010 with 0.3% $I_a$ gave a lifetime of 2700 hrs. (Item 13); 0.05% Goodrite 3114 with 0.3% $I_a$ gave a lifetime of 2100 hrs. (Item 19); 0.05% Ethyl A.O. 330 with 0.3% $I_a$ gave a lifetime of 1810 hrs. (Item 24). These lifetimes are clearly superior to those obtainable with 0.3% of a typical commercial phosphite stabilizer, Weston WX-618 in combination with the same phenolic antioxidants; lifetime of only 250 to 970 (Items 10, 18, 23) were obtained.

Table 2
Effectiveness of Antioxidants in Polyethylene

| | | Oven Life (Hour) for 65-Mil Molding 140° C. Duplicate Runs | |
|---|---|---|---|
| | Antioxidant | A | B |
| 1. | None | 35 | 20 |
| 2. | 0.1% Santonox R[1] | 190 | 260 |
| 3. | 0.1% Weston 618[2] | — | 60 |
| 4. | 0.3% Ia | — | 20 |
| 5. | 0.3% Ib | — | 20 |
| 6. | 2 + 4 | — | 640 |
| 7. | 2 + 5 | 300 | 470 |
| 8. | 2 + 3 | — | 360 |
| 9. | 3.0% Monarch 81[3] | 100 | 110 |
| 10. | 9 + 2 | 890 | 1370 |
| 11. | 9 + 6 | — | >5063 |
| 12. | 9 + 7 | >3078 | >5063 |
| 13. | 9 + 8 | — | 980 |

[1]Bis(2-methyl-5-t-butyl-4-hydroxyphenyl)sulfide (a trademark of Monsanto Co.).
[2]Distearyl pentaerythritol diphosphite (a trademark of Borg Warner Corp.).
[3]Carbon black (a trademark of Cabot Corp.).

The outstanding effectiveness of $I_a$ and $I_b$ in combination with a hindered phenolic antioxidant for stabilization of black polyethylene is seen in Table II. Neither the phenolic antioxidant alone (Item 2) nor phosphorus compounds alone (Items 3, 4, 5) provide a substantial increase in polyethylene stability. The antioxidant alone (Item 9) is a moderate stabilizer for black pigmented polyethylene, but $I_a$ and $I_b$ in combination with the hindered phenolic antioxidant (Items 11 and 12) provides oven lifetimes several times as great as those obtained with the antioxidant alone.

The invention has been described in detail with particular reference to certain preferred embodiments thereof, but it will be understood that variations and modifications can be effected within the spirit and scope of the invention.

We Claim:

1. A stabilizer combination for use in improving the resistance of olefin polymers to deterioration in physical properties on exposure to heat comprising A) from about 0.1 to about 25 parts by weight of an organic phosphonitrilic composition derived from a triphosphonitrilic halide and a hydroxy compound selected from unsubstituted saturated alcohols containing 1 to about 20 carbon atoms, and diols having the formula $$R_1CH-X-CH-R_2 \text{ with OH, OH} \quad \text{and} \quad HO+CH_2CH_2OCH_2CH_2O)_{\overline{n}}H$$

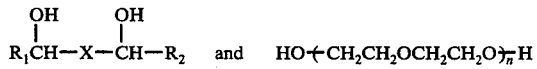

wherein X is a covalent bond or alkylene of 1 to about 12 carbon atoms, $R_1$ and $R_2$ are the same or different as hydrogen or alkyl having 1 to about 6 carbon atoms, and n is an integer from 1 to about 200; and B) from about 0.1 to about 25 parts by weight of an ortho-hindered phenolic primary antioxidant.

2. A stabilizer combination of claim 1, wherein the phosphonitrilic compound utilized is triphosphonitrilic chloride and the alcohols utilized are selected from the group consisting of ethylene glycol, polyethylene glycol and alkyl alcohols.

3. A stabilizer combination of claim 2 wherein the ortho-hindered phenol and primary antioxidant is selected from tetrakis [3-(3,5-di-tert-butyl-4-hydroxyphenyl)propionyloxymethyl]methane, distearyl pentaerythritol diphosphite, tetrakis [3-(3,5-di-tert-butyl-4-hydroxyphenyl)propionyloxymethyl]methane and 2,4,6-tris(3,5-di-tert-butyl-4-hydroxybenzyl)mesitylene, bis(2-methyl-5-t-butyl-4-hydroxyphenyl)sulfide.

4. A heat resistant stabilized polyolefin polymer containing the combination of stabilizers of claim 1.

5. A heat resistant stabilized polyolefin polymer containing the combination of stabilizers of claim 2.

6. A heat resistant stabilized polyolefin polymer containing the combination of stabilizers of claim 3.

7. A composition of claims 4, 5 and 6 in which the polyolefin is selected from polyethylene and polypropylene.

* * * * *